(12) United States Patent
Gimzewski

(10) Patent No.: US 8,501,092 B2
(45) Date of Patent: Aug. 6, 2013

(54) CALORIMETER AND METHODS OF USE THEREOF

(75) Inventor: James K. Gimzewski, Topanga, CA (US)

(73) Assignee: The Regents of the University of California, Oakland, CA (US)

(\*) Notice: Subject to any disclaimer, the term of this patent is extended or adjusted under 35 U.S.C. 154(b) by 1105 days.

(21) Appl. No.: 10/589,430

(22) PCT Filed: Apr. 14, 2005

(86) PCT No.: PCT/US2005/012730
§ 371 (c)(1),
(2), (4) Date: Jan. 30, 2007

(87) PCT Pub. No.: WO2005/114121
PCT Pub. Date: Dec. 1, 2005

(65) Prior Publication Data
US 2007/0189920 A1 Aug. 16, 2007

Related U.S. Application Data

(60) Provisional application No. 60/563,029, filed on Apr. 15, 2004.

(51) Int. Cl.
*G01N 33/00* (2006.01)
(52) U.S. Cl.
USPC ....... 422/51; 422/68.1; 422/82.01; 422/82.02
(58) Field of Classification Search
USPC ............... 422/50, 55, 56, 58, 68.1, 82.12, 99, 422/100, 51, 82.01, 82.02
See application file for complete search history.

(56) References Cited

U.S. PATENT DOCUMENTS

| | | | | |
|---|---|---|---|---|
| 5,381,101 A | * | 1/1995 | Bloom et al. | 324/676 |
| 5,970,790 A | * | 10/1999 | Jouwsma et al. | 73/204.12 |
| 6,164,140 A | * | 12/2000 | Kalinoski | 73/861.357 |
| 6,193,413 B1 | | 2/2001 | Lieberman | |
| 6,477,901 B1 | * | 11/2002 | Tadigadapa et al. | 73/861.352 |
| 6,513,969 B2 | | 2/2003 | Plotnikov et al. | |
| 6,647,778 B2 | * | 11/2003 | Sparks | 73/204.26 |
| 6,668,627 B2 | * | 12/2003 | Lange et al. | 73/105 |
| 7,387,889 B2 | * | 6/2008 | Manalis | 435/287.1 |
| 2002/0092340 A1 | * | 7/2002 | Prater et al. | 73/24.02 |
| 2004/0038426 A1 | * | 2/2004 | Manalis | 436/514 |

\* cited by examiner

*Primary Examiner* — Sam P Siefke
(74) *Attorney, Agent, or Firm* — Paula A. Borden; Bozicevic, Field & Francis LLP.

(57) ABSTRACT

The present invention provides a calorimeter device, generally comprising a reaction vessel which may be U-shaped and which may be cantilevered; and a sensor for detecting temperature changes. In various embodiments, the sensor detects heat input into or output from the reaction vessel; changes in the electrical properties of a material coated onto the reaction vessel; changes in the mechanical properties of the reaction vessel; or changes in the resonance properties of the reaction vessel. The present invention further provides arrays of a subject calorimeter device. The present invention further provides a system for detecting a temperature change. The present invention further provides methods of detecting a temperature change that occurs as a result of a chemical, biochemical, biological, light-induced, or physical process. The methods generally involve introducing a sample into a subject device, and detecting a temperature change.

13 Claims, 5 Drawing Sheets

CALORIMETER AND METHODS OF USE THEREOF

CROSS REFERENCE

This application is a national stage filing under 35 U.S.C.§371 of International Patent Application Ser. No. PCT/US2005/012730, which was filed on Apr. 14, 2005 and which was published in English under PCT Article 21(2) as WO 2005/114121 on Dec. 1, 2005, which International Patent Application claims benefit of priority of U.S. Provisional Patent Application Ser. No. 60/563,029, filed Apr. 15, 2004, which application is incorporated herein by reference in its entirety.

STATEMENT REGARDING FEDERALLY SPONSORED RESEARCH

The U.S. government may have certain rights in this invention, pursuant to grant no. NCC2-1364-4 awarded by the National Aeronautics and Space Administration.

FIELD OF THE INVENTION

The present invention is in the field of devices for measuring heat absorbed or generated from various chemical, biochemical, physical, light-induced, and biological processes.

BACKGROUND OF THE INVENTION

Microcalorimeters are devices that measure very small quantities of heat. In chemistry, biochemistry, cell biology, and pharmacology, ultrasensitive microcalorimeters are frequently used to measure thermodynamic properties of biological macromolecules, such as proteins.

Two commonly used types of microcalorimeters are the differential scanning calorimeter and the isothermal titration calorimeter. The differential scanning calorimeter automatically raises or lowers the temperature of the system at a given rate, while monitoring any temperature differential that arises between the two cells. From the temperature differential information, small differences between the amount of heat absorbed or released by the sample cell in comparison to the reference cell can be determined and attributed to the test substance.

In isothermal titration calorimetry, the instrument maintains a constant temperature while the concentration of an additional substance added to the cells is varied. The additional substance can be, e.g., a ligand that binds to the test substance in the sample cell. The instrument measures the heat absorbed or released as the newly introduced ligand binds to the test substance. By repeating the titration experiment using multiple additions of the ligand until binding is complete, various information concerning the interaction between the test substance and the ligand, e.g., stoichiometry, binding constant, and heat of binding, can be determined.

There is a need in the art for improved calorimetry devices and methods. The present invention addresses this need.
Literature
U.S. Pat. Nos. 6,513,969; 6,193,413.

SUMMARY OF THE INVENTION

The present invention provides a calorimeter device, generally comprising a reaction vessel which may be U-shaped and which may be cantilevered; and a sensor for detecting temperature changes. In various embodiments, the sensor detects heat input into or output from the reaction vessel; changes in the electrical properties of a material coated onto the reaction vessel; changes in the mechanical properties of the reaction vessel; or changes in the resonance properties of the reaction vessel. The present invention further provides arrays of a subject calorimeter device. The present invention further provides a system for detecting a temperature change. The present invention further provides methods of detecting a temperature change that occurs as a result of a chemical, biochemical, biological, light-induced, or physical process. The methods generally involve introducing a sample into a subject device, and detecting a temperature change.

DEFINITIONS

Figure 1:
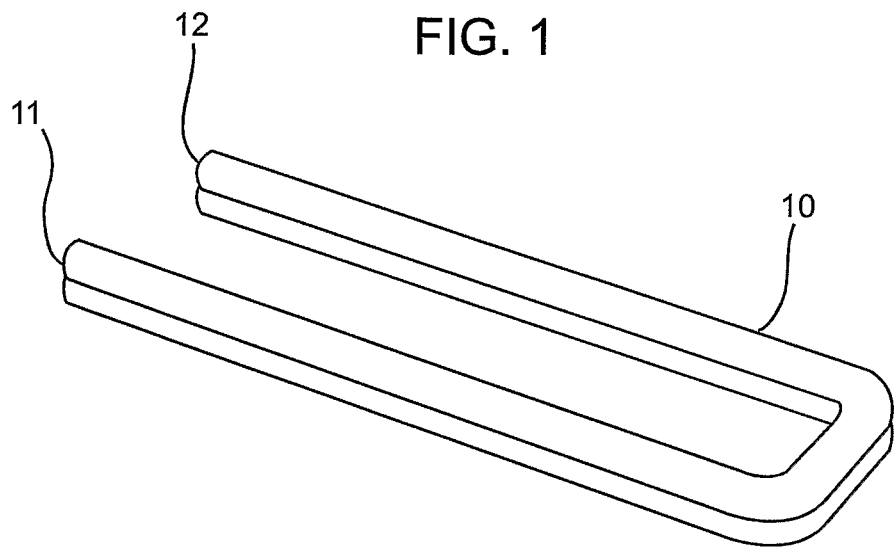
FIG. 1 depicts an exemplary embodiment of a subject device.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a reaction" includes a plurality of such reactions and reference to "the device" includes reference to one or more devices and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

A "computer-based system" refers to the hardware means, software means, and data storage means used to analyze information. The minimum hardware of a subject computer-based system comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" or "computing means" references any hardware and/or software combination that will perform the functions required of it. For example, any processor herein may be a programmable digital microprocessor such as available in the form of an electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

DETAILED DESCRIPTION OF THE INVENTION

The present invention provides a calorimeter device, generally comprising a reaction vessel (also referred to herein as "calorimeter vessel," "calorimeter tube," "fluidic channel," or "tube"), which reaction vessel may be U-shaped; and a sensor for detecting temperature changes. In various embodiments, the sensor detects heat input into or output from the reaction vessel; changes in the electrical properties of a material coated onto the reaction vessel; changes in the mechanical properties of the reaction vessel; or changes in the resonance properties of the reaction vessel. The present invention further provides arrays of a subject calorimeter device. The present invention further provides methods of detecting a temperature change that occurs as a result of a chemical, biochemical, biological, light-induced, or physical process. The methods generally involve introducing a sample into a subject device, and detecting a temperature change in the device, which temperature change is representative of a calorimetric effect of the process involving the sample.

Calorimeter Device

The present invention provides a calorimeter device, generally comprising a reaction vessel (which may be U-shaped, and which in some embodiments is cantilevered); and a sensor for detecting a temperature change in the reaction vessel. A subject calorimeter device is useful for detecting temperature changes that occur during the course of various processes, including a chemical reaction, a biochemical reaction, a biological event, a light-induced process, and a physical process.

The temperature change is in some embodiments detected by a change in mechanical property of the reaction vessel, e.g., by detecting bending of the reaction vessel. The temperature change is in other embodiments detected by changes in electrical properties of a layer coating the reaction vessel. The temperature change is in other embodiments detected by a change in resonance properties of the reaction vessel. The temperature change is in other embodiments detected by the heating or cooling necessary to maintain the tube at a constant temperature; the heat applied or decreased is a direct measure of the heat evolved or absorbed by the chemical, light-induced, biological, biochemical, or physical process occurring in the liquid.

The reaction vessel is a thin-walled, low-volume enclosure through which one or more liquids can be injected. The reaction vessel includes an inlet and an outlet. A sample is introduced into the inlet. Typically, the reaction vessel is in the form of a tube or other fluidic channel. The shape of the tube or other channel generally provides for laminar flow of a liquid through the tube. Typically, the reaction vessel is mounted on a support, where the support points are generally at the inlet and the outlet of the reaction vessel. The reaction vessel is shaped such that the above-noted changes (e.g., mechanical bending, changes in electrical properties, changes in resonance frequency, etc.) can be detected. As such, suitable shapes include, but are not limited to, a U-shaped configuration.

The reaction vessel has at least a minimum length such that the inlet and outlet can be mounted onto the same surface of a support (e.g., a support block). As such, the reaction vessel generally has a length of from about 0.5 cm to about 2 cm.

The reaction vessel has an inner diameter of from about 10 µm to about 1 mm, e.g., from about 10 µm to about 50 µm, from about 50 µm to about 100 µm, from about 100 µm to about 500 µm, or from about 500 µm to about 1 mm.

The total volume capacity of the reaction vessel is in a range of from about 1 µl to about 1 ml, e.g., from about 1 µl to about 10 µl, from about 10 µl to about 100 µl, from about 100 µl to about 500 µl, or from about 500 µl to about 1 ml.

The reaction vessel wall is thin, e.g., in a range of from about 1 µm to about 1 mm, e.g., from about 1 µm to about 10 µm, from about 10 µm to about 100 µm, from about 100 µm to about 500 µm, or from about 500 µm to about 1 mm.

A subject device detects temperature changes in the pico-Joule (pJ) range. For example, a subject device detects temperature changes in the range of from about 1 pJ to about 1000 pJ, e.g., from about 1 pJ to about 10 pJ, from about 10 pJ to about 50 pJ, from about 50 pJ to about 100 pJ, from about 100 pJ to about 200 pJ, from about 200 pJ to about 250 pJ, from about 250 pJ to about 500 pJ, from 500 pJ to about 750 pJ, or from about 750 pJ to about 1000 pJ.

The reaction vessel comprises materials that do not react with, or interfere with, any process taking place in the reaction vessel, e.g., the materials are generally inert. In many embodiments, the reaction vessel comprises a material such a silicon, a silicon nitride, and the like. In some embodiments, the reaction vessel comprises one layer of material. In some embodiments, the reaction vessel comprises two or more layers of materials.

In some embodiments, the reaction vessel comprises a layer that functions as a sensor ("a sensor layer") to determine the temperature of the reaction vessel, or to act as an actuated thermo-mechanical transducer. In other embodiments, the reaction vessel comprises a layer that functions as a sensor, such that a temperature change is detected as a change in the electrical properties of the layer. In some embodiments, the layer is a bimetallic layer or other material that bends in response to a change in temperature. In some embodiments, the material is a shape-memory material (e.g., a nickel-titanium alloy; NITINOL).

In some embodiments, the sensor layer is a thermistor. Suitable thermistors include those with a negative resistance/temperature coefficient (NTC) and those with a positive resistance/temperature coefficient (PTC). NTC thermistors include those manufactured from the oxides of the transition metals, e.g., manganese, cobalt, copper and nickel. PTC thermistors include those manufactured from barium titanate and strontium titanate. Suitable NTC and PTC thermistors and thermistor materials include those discussed in U.S. Pat. Nos. 6,607,679, 6,218,928, and 6,712,771.

In some embodiments, the sensor layer is a piezoelectric material, or a piezoresistive material. These materials will produce an electric field when the material changes dimensions, e.g., when the reaction vessel bends. Piezoelectric materials are known in the art; see, e.g., "Piezoelectric Materials: Advances in Science, Technology and Applications (2000) C. Galassi et al., eds., Kluwer Academic Publishers. Suitable piezoelectric materials include quartz ($SiO_2$), barium titanate ($BaTiO_2$), ST-cut quartz, quartz crystals, piezoelectric ceramics, such as those of the barium titanate and lead zirconium titanate families, e.g., $LiNbO_3$; $BaTiO_3$; 95 wt. % $BaTiO_3$/5% $GaTiO_3$; 80 wt. % $BaTiO_3$/12% $PbTiO_3$/8% $CaTiO_3$; $PbNb_2O_6$; $Na_{0.5}K_{0.5}NbO_3$; and the like. In some cases, the sensor layer may comprise a piezoelectric coating material, such as ZnO or AlN, applied to a non-piezoelectric material, such as silicon. The piezoelectric properties of these and other suitable materials are provided in CRC Handbook of Materials Science, Vol. III, Charles T. Lynch, CRC Press: Boca Raton, 198 (1975).

Detecting Resonance

In some embodiments, the reaction vessel is embedded in a micromechanical cantilever. In some of these embodiments, the cantilever comprises two layers of materials such as silicon and aluminum.

In some embodiments, e.g., wherein the U-shaped reaction vessel is mounted in a vacuum exterior, the Q factor of the cantilever in resonance is used as a very sensitive thermal sensor. The high Q factor of the cantilever provides a means to determine the resonance frequency as well as the internal damping energy of the liquid in the tube. In this embodiment, no bimetallic layer is required. The temperature changes occurring as a result of a process taking place within the reaction vessel has two effects: first, the elongation of the tube due to change in the mass of the thermally expanded liquid will change the resonance frequency. Likewise, the viscosity of water changes by approximately 0.2% per degree Celsius. This will change the Q factor. Other processes occurring within the tube, such as nucleic acid hybridization, can also influence the Q-factor and resonance properties of the resonating tube.

Detecting Temperature Changes

In some embodiments, the sensor detects a change in temperature in the reaction vessel. In some of these embodiments, isothermal conditions are maintained by use of an integrated heating device. The integrated heating device in some embodiments also functions as a temperature sensing element and/or a thermo-mechanical transducer.

In some embodiments, the reaction vessel is heated by application of an electrical current through a coating layer. The reaction vessel is heated or cooled to maintain a constant temperature. The amount of heat applied or decreased is a direct measure of the heat evolved or absorbed during the process taking place in the reaction vessel. Thus, e.g., where the process taking place in the reaction vessel generates heat, the amount of heat generated during the process is determined by the degree of cooling necessary to maintain the reaction vessel at a constant temperature. Conversely, where the process taking place in the reaction vessel absorbs heat, the amount of heat absorbed during the process is determined by the amount of applied heat required to maintain the reaction vessel at a constant temperature.

In some embodiments, the device is enclosed in a vacuum environment, to minimize convection and/or conduction heat losses that would occur in atmospheric conditions.

Detecting Changes in Mechanical Properties of the Reaction Vessel

In some embodiments, a temperature change in the reaction vessel is detected by changes in mechanical properties of the reaction vessel. For example, in some embodiments, the reaction vessel bends in response to a temperature change in the reaction vessel. In these embodiments, the reaction vessel comprises one or more materials that bend in response to a temperature change. Such materials are well known to those skilled in the art and include, but are not limited to, piezoresistive materials, bimetallic materials, and the like. Such a micromechanical sensor can be provided where the reaction vessel is coated with metal on one side, which metal undergoes bending due to differential thermal expansion of the coating metal and the material onto which the sensor layer is coated (the "bimetallic effect"). Thus, in many embodiments, the coating layer comprises a thermal sensitive material.

Sensors to detect a mechanical response to a temperature change include, but are not limited to, capacitative sensing, piezoelectric effect, beam deflection, interferometric sensing methods, optical beam reflection, and electron tunneling sensors.

Figure 3A:
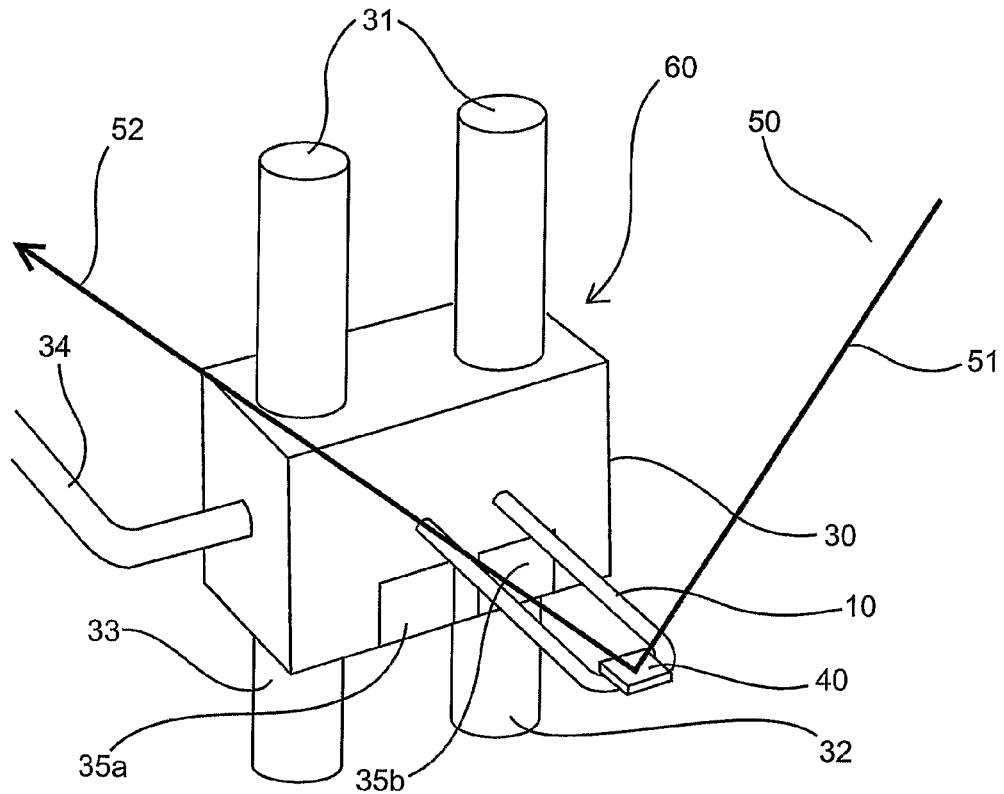
FIG. 3A depicts an exemplary embodiment of a subject device, in which the reaction vessel is mounted on a block that thermalizes the liquid entering the vessel.
Figure 4:
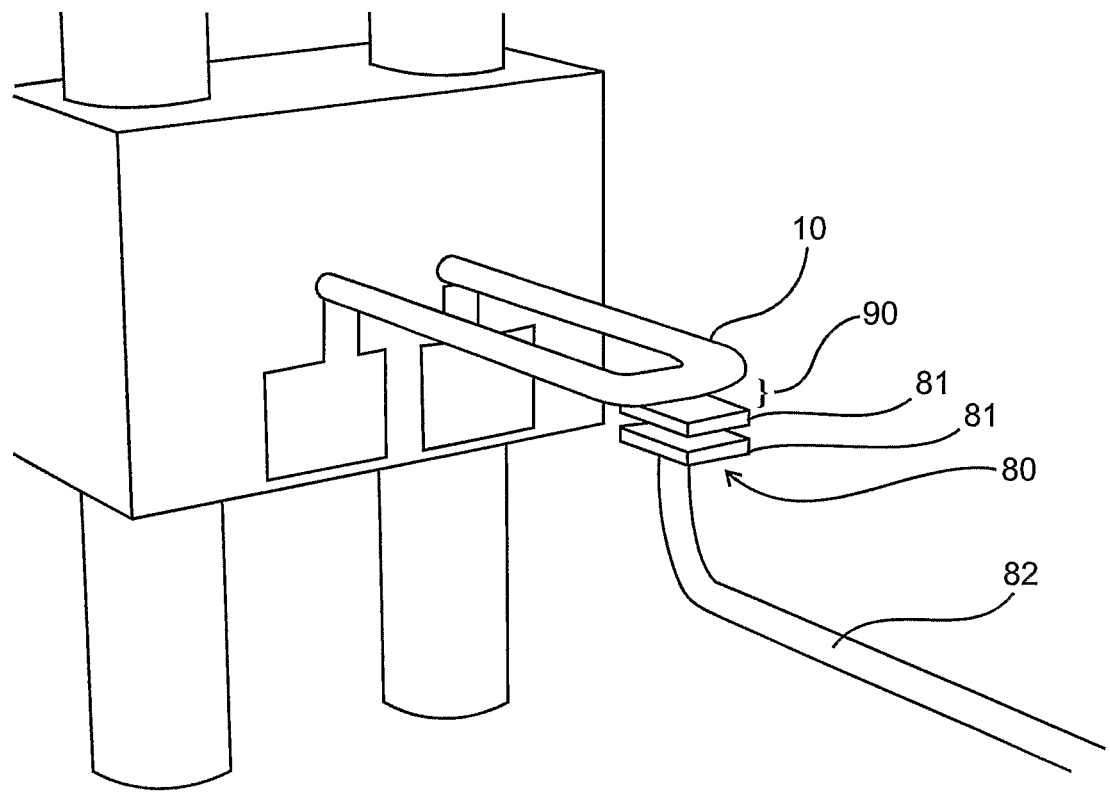
FIG. 4 depicts an exemplary embodiment of a subject device, in which two electrodes form a capacitor that is used to determine the bending of the reaction vessel.

Non-limiting examples of these embodiments are depicted in FIGS. 3A and 4. For example, in some embodiments, a subject device comprises a reflector mounted on the reaction vessel, where the reflector (e.g., a mirror) reflects a beam of incident light. Movement of the mirror in response to a temperature change in the reaction vessel is detected by a sensor which detects the reflected beam of light.

In these embodiments, light, e.g., a laser beam, is directed onto a mirror mounted on the reaction vessel, and the position of a reflected laser beam is detected by a sensor. For example, a first position of a laser beam reflected by a mirror mounted on the reaction vessel is detected at a first time; and a second position of a laser beam reflected by the mirror is detected at a second time. Where the second position differs substantially from the first position indicates bending of the reaction vessel, and hence indicates a change in temperature in the reaction vessel.

Measurements temperature changes in the vessel are made at regular intervals (e.g., every 5 seconds, 10 seconds, 20 seconds, 30 seconds, 60 seconds, two minutes, 5 minutes, 10 minutes, 15 minutes, etc.); or substantially continuously. Alternatively, measurements of temperature changes in the vessel are made at a single time point, or at random time points.

Suitable sensors for detecting a reflected beam of light include any device that is capable of detecting a reflected beam of light. Suitable sensors include, but are not limited to, charge coupled devices (CCD). The CCD camera is connected to an image analysis computer system for data storage and analysis.

In other embodiments, bending of the reaction vessel (indicating a temperature change within the reaction vessel) is detected by use of a capacitor (see, e.g., FIG. 4). For example, a thin, flat surface mounted on the reaction vessel functions as one side of an electrical capacitor for distance determination (e.g., measuring bending of the reaction vessel). In operation, the bending of the tube is kept constant by adjusting the applied heating power, which is absorbed by the calorimeter tube.

Detecting Changes in Electrical Properties of the Coating Layer of the Reaction Vessel In some embodiments, a temperature change is detected by detecting an electrical change in a material layered onto the reaction vessel. Suitable materials include piezoelectric materials and piezoresistive materials, as discussed above.

Mixing

Mixing of reactants in the reaction vessel can be achieved by any of a variety of means. As one non-limiting example, reactants A and B are injected into the inlet of a reaction vessel; reactants A and B do not mix due to turbulence, but instead exhibit laminar flow. In this example, the reaction is diffusion controlled. The tube can be patterned to control mixing. Alternatively, turbulence can be introduced into the tube to effect mixing.

Mixing can also be achieved by increasing the flow speed exceeding the Reynolds number for turbulent flow. Optimal flow conditions can be determined by observing the mixing of liquid dyes. Injected reactants can also be pulsed in the tube.

Exemplary Embodiments

FIGS. 1-5 depict exemplary embodiments of a subject device. FIG. 1 depicts a reaction vessel in the form of a tube 10 or other fluidic channel, supported at one or more points. Tube 10 has inlet 11 into which a liquid comprising one or more reactants, cells, biomolecules, etc. can be injected; and outlet 12. The liquid in the tube may change temperature due to a variety of processes such as a chemical reaction, a biochemical reaction, a biological reaction, or a light-induced process. A sensor detects a temperature change. In various embodiments, the sensor detects heat input or output; changes in the electrical properties of a material coated onto the inner surface of the reaction vessel; or changes in the mechanical properties of the reaction vessel. In many embodiments, the temperature change is determined from a coating layer that introduces bending via a bimetallic process. In other embodiments, the temperature change is determined from a coating layer that functions as a thermistor. In some embodiments, the reaction vessel is heated by application of an electrical current through the coating layer. In many embodiments, the reaction vessel is heated or cooled to maintain a constant temperature; or the current is changed to maintain a constant deflection or thermistor resistance. The heat applied or decreased in this way is a direct measure of the heat evolved or absorbed by the process (chemical process, physical process, biological process, etc.) occurring in the liquid.

Figure 2:
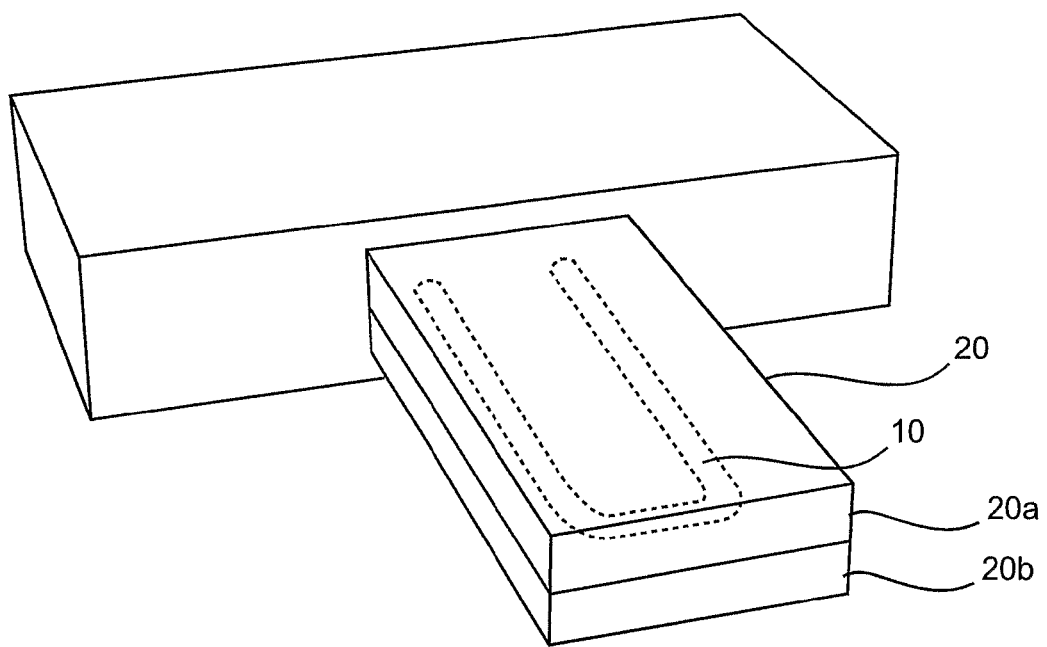
FIG. 2 depicts an exemplary embodiment of a subject device, in which the reaction vessel is embedded in a micromechanical cantilever.

FIG. 2 depicts an exemplary embodiment of the invention, in which the U-shaped reaction vessel 10 is embedded in, or formed within, a micromechanical cantilever structure 20 made from two layers of material, e.g., a first layer 20a of a material such as silicon (Si) and a second layer 20b of a material such as aluminum (Al).

Figure 3B:
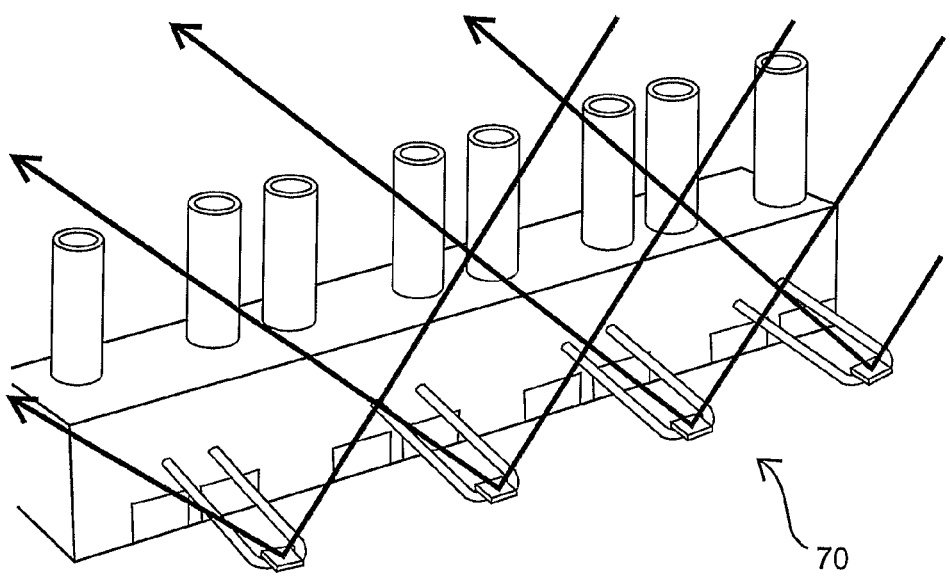
FIG. 3B depicts an exemplary subject array.

FIG. 3A depicts an exemplary embodiment of the invention, in which the U-shaped reaction vessel 10 is mounted on a block 30 that thermalizes the liquid entering the reaction vessel. Two inlet lines 31 are mounted on top of the block; and an outlet line 32 and flush line 33 are mounted below. The block contains a micro valve system that opens and closes the inlet lines, where the valve system is coupled to a flowmeter which is controlled by an electrical signal line 34. A small mirror 40 on the end of the tube 10 is used in conjunction with standard beam deflection techniques to measure the beam deflection. Contact pad 35a for thermistor, for interconnection to a temperature detection system, and contact pad 35b for bimetallic heating, for interconnection to a temperature control system, are positioned near the reaction vessel. A laser beam 50 is shown, with incident beam 51 transmitted from a light source, and reflected beam 52 reflected by mirror 40. As shown in FIG. 3B, the device 60 is in some embodiments provided in an array 70, which enables references, standards, and other differential modes of operation in parallel.

FIG. 4 depicts an exemplary embodiment of the invention, in which two electrodes 81 form a capacitor 80 which is used to detect bending of the tube 10. The electrical heater element 82 is adjusted to maintain a constant gap 90. The charge in the capacitor will vary depending on deflection of the reaction vessel 10, where an electrical signal representative of the charge is fed back to a control system, which in turn adjusts the physical position of the capacitor relative to tube 10 and capacitor surface.

Figure 5:
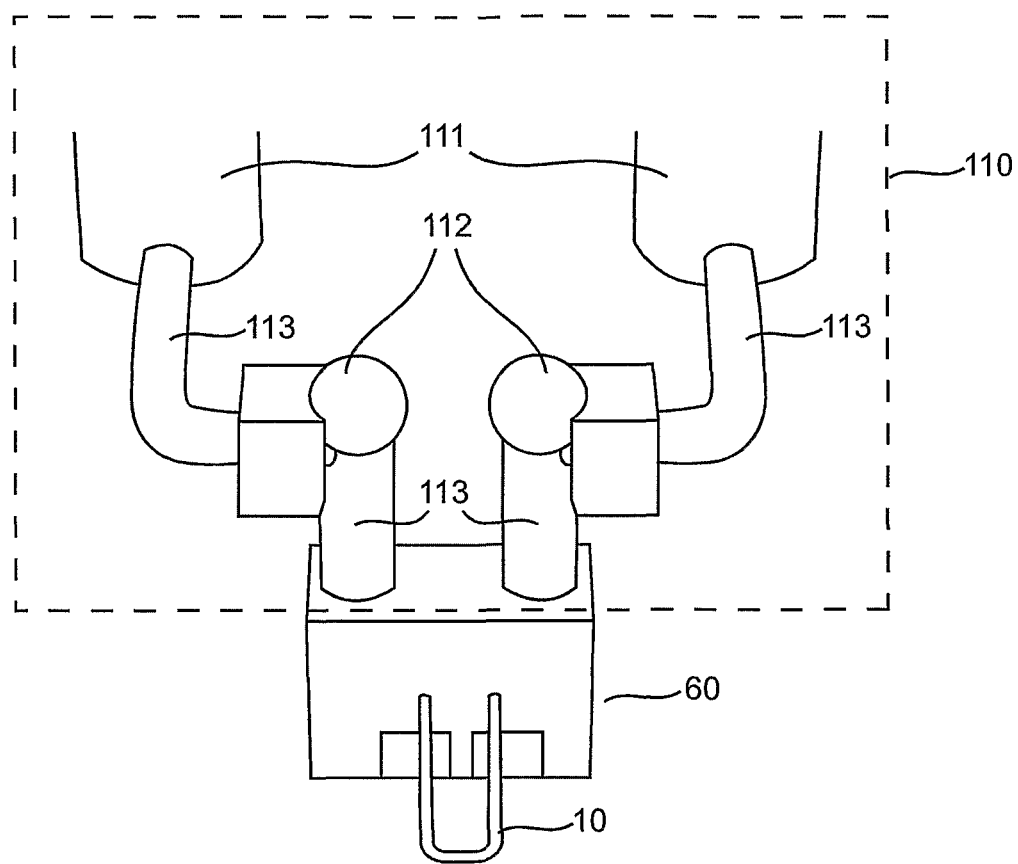
FIG. 5 depicts an exemplary embodiment of a subject system that includes two reservoirs of liquid and valves for automated analyses.

FIG. 5 depicts an exemplary embodiment of the invention, in which a subject system includes a device 60 and a fluid control system 110, where the fluid control system is in fluid communication with the reaction vessel 10. Fluid control system 110 includes two reservoirs 111 of liquid; valves 112 for regulating the volume, rate, and/or pressure of the flow of fluid from the reservoirs to the reaction vessel; and conduits 113 interconnecting the reservoirs, the valves, and the reaction vessel, and providing for fluid connection therebetween.

Arrays

The present invention further provides arrays of a subject calorimeter device. An array comprises a plurality of a subject device, e.g., two, three, four, five, six, seven, eight, nine, ten, from 10 to 25, from 25 to 50, or from 50 to 100, or more, subject devices. In many embodiments, a subject array includes a reference reaction vessel; and one or more standards, e.g., where one or more subject devices provide for generating a standard curve against which to evaluate the results from a test sample. An array is provided in any of a variety of configurations.

A subject array is useful for screening a variety of compounds, e.g., in the setting of proteomic analyses; small molecule drug discovery; and the like.

Systems

The present invention further provides a system for detecting temperature change in a process. A subject system includes a subject device (which is in some embodiments an array of a subject device); and one or more of a control system; a data management system; and a user interface system.

Control Systems

Control systems which may be included in a subject system include, but are not limited to, a power source; a fluid flow control system; a light source; a light detection system; a temperature control system; and a temperature detection system. A fluid flow control system may include one or more of a pump; a reservoir; a valve, for controlling the volume, rate, and/or pressure of a fluid, e.g., from a reservoir to a reaction vessel; etc.

In some embodiments, a subject system comprises a means for detecting a reflected light beam, such as a CCD (e.g., an array of CCD); e.g., where the subject device comprises a mirror (a reflector) mounted on the reaction vessel. In other embodiments, a subject system comprises a means for detecting bending of the reaction vessel, e.g., a capacitor.

Data Management Systems

In some embodiments, a subject system comprises a subject device (or array of devices); and a data management system. Data management systems may comprise one or more of a data collection means; a data storage means; and a data analysis means. In some embodiments, a subject system comprises a subject device; a data storage means for storing data generated by the device; and a data analysis means for analyzing the data generated by the device. Data analysis can be performed by a computer program product. The present invention thus provides system that includes computer program product including a computer readable storage medium having a computer program stored on it. The program can, when read by a computer, execute analysis of the temperature change data generated by the device (or array of devices). The computer program product has stored therein a computer program for performing the analysis.

The computer program can be recorded on computer readable media, e.g., any medium that can be read and accessed directly or indirectly by a computer. Such media include, but are not limited to: magnetic tape; optical storage such as compact disc-read only memory (CD-ROM) and digital versatile disk (DVD); electrical storage media such as random access memory (RAM) and read-only memory (ROM); and hybrids of these categories such as magnetic/optical storage media. One of skill in the art can readily appreciate how any of the presently known computer readable media can be used to create a manufacture that includes a recording of the present programming/algorithms for carrying out the above-described methodology. In certain embodiments, the system further provides a user interface, where the user interface presents to a user the option of selecting among one or more different, including multiple different, criteria. The instructions may include installation or setup directions. The instructions may include directions for use of the invention.

User Interface

In some embodiments, a subject system comprises a subject device (or a subject array); and a user interface. A user interface may include one or more of a data input means (e.g., a keyboard, a mouse); a display (e.g., a computer monitor), e.g., for displaying data output.

Utility

A subject device is useful for detecting temperature changes that occur during the course of various processes, including a chemical reaction, a biochemical reaction, a biological event, a light-induced process, and a physical process. The temperature change that occurs is a readout for the chemical reaction, biochemical reaction, biological event or status, light-induced process, or physical process.

In some embodiments, a subject calorimeter device is used as a photothermal spectrophotometer or IR-spectrophotometer, based on the thermal signal generated by infrared (IR), visible, or ultraviolet (UV) absorption.

A subject device enables the variations in thermal properties such as a phase transition, by ramping the temperature Differential Scanning Calorimetry. The pressure applied in the tube can be used in combination with the above methods to examine folding properties of large biopolymers.

A subject device is useful for detecting chemical reactions. A subject device is useful for detecting biochemical reactions. A subject device is useful for detecting binding of a small molecule to a macromolecule (e.g., a polypeptide, a polynucleotide, a polysaccharide, a lipid). For example, binding of a small molecule (e.g., a molecule having a molecular weight in the range of from about 50 daltons to about 5,000 daltons, or from about 50 daltons to about 2,5000 daltons) to a polypeptide (e.g., a receptor, an enzyme, and the like) is useful for identifying agents (e.g., pharmaceutically active agents) that modulate (e.g., increase or decrease) the activity of a polypeptide. A subject device is useful for detecting binding between two macromolecules. For example, a subject device is useful for detecting nucleic acid hybridization; for detecting binding of a protein to a nucleic acid; for detecting binding of two proteins to one another; etc.

Determining a Characteristic of a Macromolecule

In some embodiments, the invention provides a method of determining a characteristic of a macromolecule, the method involving introducing the macromolecule into the reaction vessel of a subject device; and detecting a temperature change in the reaction vessel. The characteristic is in some embodiments protein conformation, where the protein conformation in various solvents, or in the presence of various analytes or other macromolecules, is determined. The characteristic is in some embodiments binding to a small molecule or binding to a macromolecule or a cell. The characteristic is in some embodiments a biological function, e.g., enzymatic activity, in the presence of various solvents, analytes, agonists, antagonists, or macromolecules.

Detecting Cancerous Cells

When cells become cancerous and metastasize, the mechanical properties of their membranes changes. The present invention provides a method of detecting mechanical properties of mammalian cells. Cells flowing through a reaction vessel in a subject device in a vacuum; the frequency-dependent resonance and Q factor are recorded; and the Q factor provides an indication of the local damping of the cell.

The cells are pumped in laminar flow through the tube one by one. An optical detector senses a cell entering the inlet of the tube when the cell is at the apex of the U-shaped tube and when it exits. Three optical sensors are used. The tube is in a vacuum environment and is mechanically vibrated over a range of frequencies ($H_2 \rightarrow 100$ $Kh_2$). The mechanical response is measured from the motion of the tube capability piezo electrically or optically.

The power spectrum then provides the Q factor of the medium in the tube, scans are made when the cell is detected at the apex, the other two sensors coupled with flow control ensure only one cell is measured at a time. Cancerous cells are diverted by standard cell sorting techniques from healthy ones. The device can also be used to study the action of drugs that "harden" (e.g., return the cell to a non-cancerous state) cancerous cells but not adversely affect or otherwise influence healthy ones.

Many other uses are possible, e,g., therapy where, e.g., cells taken from an individual are treated, then returned to the individual.

The invention further provides a method of treating a disease or disorder. The methods generally involve identifying a cancerous cell using a subject method; and reconmmending a treatment regimen appropriate to the abnormality.

For example, where a cell in a tissue biopsy is determined to be a cancerous cell, a treatment regimen appropriate to the particular type of cancer is recommended. In some embodiments, the methods provide for staging of the cancer. A course of chemotherapy or radiation therapy appropriate to the stage of the cancer is then recommended.

Detecting the Presence of an analyte

The invention further provides assays for detecting the presence of an analyte in a test sample. The methods generally involve contacting a molecular entity (e.g., a polypeptide, a polynucleotide, a carbohydrate, a polysaccharide) with a test sample; and detecting any change in the temperature of the reaction vessel in response to an interaction between the molecular entity and the test sample. Such a screening assay is useful to detect the presence in a sample of an analyte suspected to exist in the sample, e.g., a subject screening assay can be used to detect the presence in a sample of a toxin or a toxic bacterium, e.g., an environmental agent (e.g., a pesticide, an herbicide, an environmental toxin, and the like), an agent of chemical or biological warfare (e.g., nerve gas, anthrax, etc.).

Assays of the invention include controls, where suitable controls include a sample (e.g., an analyte) in the absence of the test sample. Generally a plurality of assay mixtures is run in parallel with different known concentrations of the analyte being detected to obtain a differential response to the various concentrations. Typically, one of these concentrations serves as a negative control, i.e. at zero concentration or below the level of detection. The assay methods provide for qualitative (e.g., presence or absence), semi-quantitative, and quantitative detection of analyte.

Screening Assays

The invention provides screening assays for identifying agents that have pharmaceutical activity. The methods generally involve introducing a test agent and a second compound into the reaction vessel of a subject device; and determining the change if any, in the temperature of the liquid in the reaction vessel. The invention further provides assays for detecting the presence of an analyte in a test sample. The methods generally involve contacting a molecular entity (e.g., a polypeptide, a polynucleotide, a ligand, etc.) or a cell with a test sample; and detecting any change in temperature in the reaction vessel in response to the test sample. A change in the temperature in the reaction vessel is indicative of a reaction between a test agent and a macromolecule (e.g., a polypeptide such as an enzyme, a receptor, etc.; a polynucleotide; a polysaccharide; a glycoprotein; a lipoprotein; etc.). In some embodiments, a test sample includes a test agent, a substrate for an enzyme, and an enzyme; and the effect of the test agent on the activity of the enzyme on the substrate is determined by detecting a temperature change compared to a control sample in the absence of the test agent. In some embodiments, a test sample includes a test agent and a cell expressing a receptor; and the effect of the test agent on activating the receptor is determined by detecting a temperature change in the test sample compared to a control sample in the absence of the test agent, or compared to a control sample in the absence of the test agent and in the presence of a ligand for the receptor. In some embodiments, a test sample includes a test agent, and a cell expressing a receptor, and a ligand (e.g., an agonist) for the receptor; and the antagonist effect of the test agent on the receptor is determined by detecting a temperature change in the test sample compared to a control sample in the absence of the test agent and in the presence of the ligand for the receptor.

The terms "candidate agent," "agent," "substance," and "compound" are used. interchangeably herein. Test agents encompass numerous chemical classes, typically synthetic, semi-synthetic, or naturally-occurring inorganic or organic molecules. Test agents may be small organic compounds having a molecular weight of more than 50 and less than about 2,500 daltons, or less than about 5,000 daltons. Test agents may comprise functional groups necessary for structural interaction with proteins, particularly hydrogen bonding, and may include at least an amine, carbonyl, hydroxyl or carboxyl group, and may contain at least two of the functional chemical groups. The test agents may comprise cyclical carbon or heterocyclic structures and/or aromatic or polyaromatic structures substituted with one or more of the above functional groups. Test agents are also found among biomolecules including peptides, saccharides, fatty acids, steroids, purines, pyrimidines, derivatives, structural analogs or combinations thereof.

Test agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.). Alternatively, libraries of natural compounds in the form of bacterial, fungal, plant and animal extracts are available from Pan Labs (Bothell, Wash.) or are readily producible. Additionally, natural or synthetically produced libraries and compounds are readily modified through conventional chemical, physical and biochemical means, and may be used to produce combinatorial libraries. Libraries of test agents also include cDNA libraries, e.g., expression libraries from a given cell type, from a cell in response to an agent, from a cell of a given physiological status (e.g., a cancerous cell), and the like.

Known pharmacological agents may be subjected to directed or random chemical modifications, such as acylation, alkylation, esterification, amidification, etc. to produce structural analogs. New potential therapeutic agents may also be created using methods such as rational drug design or computer modeling.

Assays of the invention include controls, where suitable controls include a sample (e.g., a cell sample; an enzyme; a polypeptide; a receptor; a polynucleotide) in the absence of the test agent. Generally a plurality of assay mixtures is run in parallel with different agent concentrations to obtain a differential response to the various concentrations. Typically, one of these concentrations serves as a negative control, i.e. at zero concentration or below the level of detection.

Agents that have an effect in an assay method of the invention may be further tested for cytotoxicity, bioavailability, and the like, using well known assays. Agents that have an effect in an assay method of the invention may be subjected to directed or random and/or directed chemical modifications, such as acylation, alkylation, esterification, aridification, etc. to produce structural analogs. Such structural analogs include those that increase bioavailability, and/or reduced cytotoxicity. Those studied in the art can readily envision and generate a wide variety of structural analogs, and test them for desired properties such as increased bioavailability and/or reduced cytotoxicity and/or ability to cross the blood-brain barrier.

The components of the assay mixture are added (e.g., injected into the reaction vessel) in any order that provides for the requisite binding or other activity. Incubations are performed at any suitable temperature, typically between 4° C. and 40° C. Incubation periods are selected for optimum activity, but may also be optimized to facilitate rapid high-throughput screening. Typically between 0.1 and 1 hour will be sufficient.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A calorimetric device comprising
a) a U-shaped calorimeter tube comprising Silicon and having an inlet end and an outlet end, and mounted onto a support at the inlet end and the outlet end, wherein the calorimeter tube comprises a coating layer comprising Aluminum, wherein the calorimeter tube bends in response to a temperature change in the calorimeter tube due to different thermal expansions of the calorimeter tube and the coating layer;
b) a capacitive sensor that detects the bending of the calorimeter tube due to different thermal expansions of the calorimeter tube and the coating layer; and
c) an integrated heating device that provides current through the coating layer to heat the calorimeter tube and maintain a substantially constant temperature based on detected bending of the calorimeter tube due to the different thermal expansions of the calorimeter tube and coating layer.

2. The device of claim 1, wherein the device detects temperature changes in the range of from about 1 pJ to about 1000 pJ.

3. The device of claim 1, wherein the calorimeter tube has a total volume capacity in a range of from about 1 µl to about 1 ml.

4. The device of claim 1, wherein the calorimeter tube is enclosed in a vacuum.

5. A method of detecting a temperature change that occurs in a process, the method comprising
introducing a sample comprising a chemical reactant, a biological entity, or a macromolecule into the device of claim 1; and
detecting a bending of the calorimeter tube with the capacitive sensor based on a temperature change in the calorimeter tube and different thermal expansions of the calorimeter tube and the coating layer; and
providing current through the coating layer to heat the calorimeter tube and maintain a substantially constant temperature based on the detected bending of the calorimeter tube due to the different thermal expansions of the calorimeter tube and coating layer.

6. The method of claim 5, wherein the process is selected from a chemical reaction, a biochemical reaction, a binding reaction, a physical process, a light-induced process, and a biological reaction.

7. A calorimetric device comprising
a) a U-shaped reaction vessel comprising Silicon and having an inlet and an outlet, and mounted onto a support at or near the inlet and the outlet, wherein the reaction vessel comprises a coating layer comprising Aluminum, wherein the reaction vessel bends in response to a change in temperature in the reaction vessel due to different thermal expansion of the reaction vessel and the coating layer;
b) a capacitive sensor that detects the bending of the reaction vessel due to different thermal expansions of the reaction vessel and the coating layer; and
an integrated heating device that provides current through the coating layer to heat the reaction vessel and maintain a substantially constant temperature based on the detected bending of the reaction vessel due to the different thermal expansions of the reaction vessel and coating layer.

8. A method of detecting a temperature change that occurs in a process, the method comprising
introducing a sample comprising a chemical reactant, a biological entity, or a macromolecule into the device of claim 7; and
detecting a bending of the reaction vessel with the capacitive sensor based on a temperature change in the reaction vessel and different thermal expansions of the reaction vessel and the coating layer; and
providing current through the coating layer to heat the reaction vessel and maintain a substantially constant temperature based on the detected bending of the reaction vessel due to the different thermal expansions of the reaction vessel and coating layer.

9. The method of claim 8, wherein the process is selected from a chemical reaction, a biochemical reaction, a binding reaction, a physical process, a light-induced process, and a biological reaction.

10. The device of claim 7, wherein the reaction vessel has a total volume capacity in a range of from about 1 µl to about 1 ml.

11. The device of claim 7, wherein the reaction vessel is enclosed in a vacuum.

12. The device of claim 7, wherein the support comprises a contact to a thermistor for interconnection to a temperature detection system, and wherein the support comprises a contact pad for bimetallic heating for interconnection to a temperature control system.

13. The device of claim 12, wherein the support comprises:
an inlet line;
a valve system that opens and closes the inlet line, wherein the valve system is controlled by a flowmeter that is coupled to the valve system;
an outlet line; and
a flush line.

* * * * *

UNITED STATES PATENT AND TRADEMARK OFFICE
CERTIFICATE OF CORRECTION

| | | |
|---|---|---|
| PATENT NO. | : 8,501,092 B2 | Page 1 of 1 |
| APPLICATION NO. | : 10/589430 | |
| DATED | : August 6, 2013 | |
| INVENTOR(S) | : Gimzewski | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1330 days.

Signed and Sealed this
Twenty-seventh Day of January, 2015

Michelle K. Lee
*Deputy Director of the United States Patent and Trademark Office*